US006248360B1

(12) United States Patent
Choi et al.

(10) Patent No.: US 6,248,360 B1
(45) Date of Patent: Jun. 19, 2001

(54) COMPLEXES TO IMPROVE ORAL ABSORPTION OF POORLY ABSORBABLE ANTIBIOTICS

(75) Inventors: Seung-Ho Choi; Jeoung-Soo Lee, both of Salt Lake City, UT (US)

(73) Assignee: International Health Management Associates, Inc., Rolling Meadows, IL (US)

( * ) Notice: Subject to any disclaimer, the term of this patent is extended or adjusted under 35 U.S.C. 154(b) by 0 days.

(21) Appl. No.: 09/598,089

(22) Filed: Jun. 21, 2000

(51) Int. Cl.[7] .............................. A61K 9/34; A61K 9/14
(52) U.S. Cl. ..................... 424/487; 424/484; 424/488; 424/485; 424/464
(58) Field of Search ..................... 424/487, 423, 424/484, 488, 464, 485; 514/781

(56) References Cited

U.S. PATENT DOCUMENTS

| | | |
|---|---|---|
| 4,525,339 | 6/1985 | Behl et al. . |
| 4,722,941 | 2/1988 | Eckert et al. . |
| 5,190,748 | 3/1993 | Bachynsky et al. . |
| 5,318,781 * | 6/1994 | Shah et al. ..................... 424/455 |
| 6,004,593 | 12/1999 | Plate et al. . |
| 6,008,228 | 12/1999 | Bailey et al. . |

FOREIGN PATENT DOCUMENTS

0526862B1   2/1993   (EP) .

OTHER PUBLICATIONS

George Beskid, Joel Unowsky, Charanjit R. Behl, JoAnn Siebelist, Jacques L. Tossounian, carolyn M. McGarry, Navnit H. Shah, and Roy Cleeland: Enteral, oral, and Rectal Absorption of Ceftriaxone Using Glyceride Enhancers, Chemotherapy 34: 77–84 (1988).

* cited by examiner

Primary Examiner—Thurman K. Page
Assistant Examiner—B. Fubara
(74) Attorney, Agent, or Firm—Thorpe North & Western

(57) ABSTRACT

The present invention provides compositions and methods for increasing absorption of poorly absorbable antibiotics, particularly third generation cephalosporin antibiotics, in oral dosage solid and/or suspension forms. Specifically, the composition is comprised of a biopolymer that is preferably swellable and/or mucoadhesive, a poorly absorbable antibiotic, and a cationic binding agent contained within the biopolymer such that the binding agent is tonically bound or complexed to at least one member selected from the group consisting of the biopolymer and the antibiotic.

60 Claims, No Drawings

COMPLEXES TO IMPROVE ORAL ABSORPTION OF POORLY ABSORBABLE ANTIBIOTICS

FIELD OF THE INVENTION

The present invention is related to compositions and methods for improving or promoting the intestinal absorption of poorly absorbable antibiotics, particularly third generation cephalosporin antibiotics, in oral dosage forms such that the antibiotics may be more readily absorbed through the mucosal membrane of the gastro-intestinal (GI) tract.

BACKGROUND OF THE INVENTION

Antibiotics have been used for several years to successfully fight pathogenic organisms such as bacteria. As technology has advanced and the understanding of pathogens has grown, anti-infective agents have become more effective. Cephalosporins are a prime example of the advance of antibiotic technology.

Cephalosporin is the general term for a group of antibiotic derivatives of cephalosporin C, which is obtained from the fungus *Cephalosporium Acremonium*. First generation cephalosporins and most second generation cephalosporins are functional in oral dosage forms, though they may be ineffective against many forms of bacteria such as those found in typical hospital infections. However, many third generation cephalosporins, such as ceftiofur, cefixime, cefepime, cefoperazone, cefotaxime, cefpodoxime, ceftazidime, ceftizoxime, ceftriaxone, and moxalactam, due to their broad spectrum of activity, are effective against some bacteria strains that are resistant to many first and second generation cephalosporins.

The GI tract, particularly the small intestines, is the primary site for the absorption of nutrients and most bioactive agents. To accommodate the amount of absorption that must take place in the small intestines, the surface area is enlarged due to the presence of villi and microvilli. However, before a bioactive compound is transferred from the intestinal lumen to the blood, the compound may have to withstand degradation or deactivation by the various components of the luminal contents. Moreover, the compound may be required to pass through several absorption barriers, such as the mucous layer and the intestinal brush-border membrane. Many compounds pass these barriers easily, but there are many nutrients and bioactive agents to which these barriers are a serious obstruction.

Third generation cephalosporins, though effective against some of the more resistant bacteria, are normally poorly absorbed through the mucosal membrane of the intestines and thus, have difficulty reaching the bloodstream systemically. Therefore, these cephalosporins have been less effective when administered by routes other than parenteral to treat systemic bacterial infections. Specifically, administration of third generation cephalosporins is sometimes accomplished by infusion, but more typically by intravenous (i.v.) or intramuscular (i.m.) injections.

Some injectable antibiotics, such as ceftriaxone, can be administered as infrequently as once a day. However, other injectable bioactive agents should be given more frequently than once daily to achieve the greatest amount of effectiveness. In either case, the necessity of obtaining treatment through i.v. or i.m. injections is inconvenient, as such treatments often requires the services of doctors, nurses, or other trained technicians. Additionally, injections can be painful and cause undue physical and psychological stress to many patients.

There are several contributing factors why third generation cephalosporins and other poorly absorbable antibiotics have low absorption in the intestines after oral administration. First, these antibiotics have high ionization properties that do not allow them to readily penetrate the intestinal mucosal membrane. Second, due to relatively high hydrophilic properties, these antibiotics are generally unstable in an aqueous environment such as in gastric juices and small intestine fluids.

As third generation cephalosporins, such as ceftriaxone, and other poorly absorbable antibiotics are poorly absorbed through the mucosal membrane of the intestines, many efforts have been made to find improved compositions and methods for delivering small intestine absorbable third generation cephalosporins or other poorly absorbable antibiotics in the form of capsules, tablets, and/or suspensions that are not harmful to the body. Though ionic surfactants, such as sodium lauryl sulfate, or chelating agents such as EDTA, have been found to enhance intestinal absorption of such large molecules, these substances are known to be harmful to the mucosal membrane.

Some technologies have shown some promise in providing compositions and methods of delivering third generation cephalosporins orally with increased intestinal absorption. In U.S. Pat. No. 4,525,339, β-lactam antibiotics were shown to penetrate the mucosal membrane of the intestines by co-administering $C_2$–$C_{12}$ fatty acid mono-, di-, or triglycerides as an absorption enhancer. In U.S. Pat. No. 5,190,748, absorption of antibiotics (such as ceftriaxone) through oral and rectal routes was enhanced by utilizing a two-component absorption enhancing system. This system is comprised of an ether of a $C_6$–$C_{18}$ alcohol and a polyoxyethylene glycol together with a second component selected from the group consisting of polyoxyethylene glycol $C_6$ to $C_{18}$ glyceride esters, $C_6$ to $C_{18}$ carboxylic acids or salts thereof, and esters of two or more $C_6$ to $C_{18}$ carboxylic acids, glycerol, and a polyoxyethylene glycol. Additionally, in U.S. Pat. No. 5,318,781, absorption of antibiotics (such as ceftriaxone) through oral and rectal routes was enhanced by utilizing a two-component absorption enhancing system comprised of Laureth-12, a second component salt of capric acid and caprylic acids, and a carrier. For optimum absorption, the antibiotic containing two component enhancer system disclosed therein may include Miglyol-812, which is a capryllic/capric triglyceride. In U.S. Pat. No. 4,722,941, the permucosal absorption of various therapeutics, including antibiotics, is reported to be enhanced by the use of fatty acids and saturated or unsaturated fatty acid glycerides.

Though each of these systems described and others are somewhat effective in delivering poorly absorbable antibiotics through the mucosal membrane after oral delivery, each have drawbacks that prevent their widespread use. Some of the compositions and/or methods do not provide significant enough drug delivery concentrations through the mucosal membrane such that commercial use is practical. Additionally, other compositions and/or methods of mucosal delivery are too costly. As the benefits of third generation cephalosporins and other poorly absorbable antibiotics have become apparent, it would be desirable to provide compositions and methods for administering these poorly absorbable antibiotics orally, and thus, provide an administration route that is more convenient and cost effective to the patient, and enhances the amount of poorly absorbable antibiotic that may be absorbed by the mucosal membrane of the intestines.

SUMMARY OF THE INVENTION

Essentially, the present invention discloses compositions and methods wherein third generation cephalosporins and other poorly absorbable antibiotics may be more readily absorbed in the small intestines, even after oral delivery. Specifically, a pharmaceutical composition for oral delivery is disclosed comprising (a) a biopolymer which is preferably swellable and/or mucoadhesive when hydrated; (b) a poorly absorbable antibiotic contained within or ionically bound to the biopolymer; and (c) a metal cation ionically bound to at least one member selected from the group consisting of the biopolymer and the antibiotic.

Alternatively, a pharmaceutical composition for oral delivery is disclosed comprising (a) a biopolymer which is preferably swellable and/or mucoadhesive when hydrated; (b) a poorly absorbable antibiotic contained within or ionically bound to the biopolymer; and (c) a cationic molecule selected from the group consisting of cationic polymers, basic amino acids, quaternary ammonium salts, and combinations thereof, wherein the cationic molecule is ionically bound to at least one member selected from the group consisting of the biopolymer and the antibiotic.

Additionally, a method of delivering a poorly absorbable antibiotic to the blood stream of an animal is disclosed comprising the steps of (a) orally administering to the animal a composition comprising a biopolymer, an effective amount of a poorly absorbable antibiotic contained within or ionically bound to the biopolymer, and a cationic binding agent ionically bound to at least one member selected from the group consisting of the biopolymer and the antibiotic; (b) causing the biopolymer to swell and adhere to a mucosal membrane lining of an intestinal wall of the animal; and (c) delivering the antibiotic from the composition to the mucosal membrane lining such that the antibiotic, and optionally the binding agent, cross the intestinal wall and enter the bloodstream.

DETAILED DESCRIPTION OF THE INVENTION

Before the present invention is disclosed and described, it is to be understood that this invention is not limited to the particular process steps and materials disclosed herein, as such process steps and materials may vary to some degree. It is also to be understood that the terminology used herein is used for the purpose of describing particular embodiments only and is not intended to be limiting as the scope of the present invention will be limited only by the appended claims and equivalents thereof.

As used herein the following terms shall have the assigned meanings:

It must be noted that, as used in this specification and the appended claims, singular forms of "a," "an, " and "the" include plural referents unless the content clearly dictates otherwise.

"Biocompatible" shall mean any substance that is not toxic to the body.

"Biodegradable" shall mean that the biopolymer used can break down or degrade within the body to non-toxic components before, after, or while an antibiotic is released.

"Poorly absorbable antibiotic" shall mean any antibiotic that exhibits low bioavailability in oral or other non-parenteral dosage form, typically due to relatively high hydrophilicity and/or ionization properties of the antibiotic. Though not required, the preferred antibiotics for use with the present invention are typically poorly absorbable due to the presence of an ionic electrical charge under physiological conditions. The antibiotic can be positively charged, negatively charged, or amphiphilic. Examples of typical poorly absorbable antibiotics that are charged include third generation cephalosporins, though other poorly absorbable antibiotics are also functional with the present invention. The charge on the antibiotic creates difficulty for the antibiotic to cross the mucosal membrane of the intestines alone. Thus, the ability for the antibiotic to cross the mucosal membrane is significantly enhanced when present as part of a composition of the present invention.

"Oral absorption" is used in the context of how the compositions of the present invention are delivered and absorbed into the blood. Typically, the composition is administered orally and the antibiotic of the composition then crosses a mucosal membrane of the gastro-intestinal tract, preferably in the intestines. However, other methods of contacting the compositions of the present invention with the mucosal membrane of the gastro-intestinal tract may be used.

"Metal ion" or "metal cation" shall mean any positively charged metal ion that is functional for use with the present invention. Essentially, the metal cation binds to the antibiotic and/or the biopolymer in accordance with the present invention. In the case of the poorly absorbable antibiotic, the metal cation may be complexed, chelated, or ionically bound to the antibiotic. Exemplary metal cations include, but are not limited to calcium, potassium, magnesium, iron, copper, zinc, aluminum, manganese, chromium, cobalt, nickel, sodium, and combinations thereof.

"Cationic molecule" shall mean any molecule with one or more positively charged moieties that act to ionically bind to the antibiotic and/or the biopolymer. Negatively charged moieties can also be present, though this is not required. Exemplary cationic molecules include cationic polymers, basic amino acids, quaternary ammonium salts, and combinations thereof.

"Cationic binding agent" is intended to include both metal cations and cationic molecules.

"Swellable" shall mean that the biopolymers and/or compositions of the present invention have the ability to swell or enlarge, such as when hydrated.

"Mucoadhesive" shall mean any biopolymer that is capable of adhering to a mucosal membrane, particularly when hydrated.

The absorption of poorly absorbable antibiotics in the small intestines is significantly enhanced by the compositions and methods of the present invention. Essentially, by ionically binding or complexing poorly absorbable antibiotics with a biopolymer (which is preferably mucoadhesive as a swollen hydrogel) and/or a binding agent, the stability of the antibiotic is significantly enhanced and the ionic charge can be partially neutralized facilitating mucosal absorption through the intestinal wall. The intestinal absorption of these otherwise poorly absorbable antibiotics may be enhanced for both solid and suspension dosage forms.

With this in mind, a first embodiment of a pharmaceutical composition for oral delivery is disclosed comprising (a) a biopolymer which is preferably swellable and/or mucoadhesive when hydrated; (b) a poorly absorbable antibiotic contained within or ionically bound to the biopolymer; and (c) a metal cation ionically bound to at least one member selected from the group consisting of the biopolymer and the antibiotic. Such compositions can be prepared for oral dosage in solid or suspension forms.

Alternatively, a second embodiment of a pharmaceutical composition for oral delivery is also disclosed comprising (a) a biopolymer which is preferably swellable and/or mucoadhesive when hydrated; (b) a poorly absorbable antibiotic contained within or ionically bound to the biopolymer; and (c) a cationic molecule selected from the group consisting of cationic polymers, basic amino acids, quaternary ammonium salts, and combinations thereof, wherein the cationic molecule is tonically bound to at least one member selected from the group consisting of the biopolymer and the antibiotic. Such a composition can be prepared for oral dosage in solid form.

Additionally, a method of delivering a poorly absorbable antibiotic to the blood stream of an animal is disclosed which comprises the steps of (a) orally administering to the animal a composition comprising a biopolymer, an effective amount of a poorly absorbable antibiotic contained within or ionically bound to the biopolymer, and a cationic binding agent ionically bound to at least one member selected from the group consisting of the biopolymer and the antibiotic; (b) causing the biopolymer to swell and adhere to a mucosal membrane lining of an intestinal wall of the animal; and (c) delivering the antibiotic from the composition to the mucosal membrane lining such that the antibiotic, and optionally the binding agent, cross the intestinal wall and enter the bloodstream.

With each of these compositions and methods, the poorly absorbable antibiotic and binding agent can be present within a specific preferred molar ratio, though these ratios are not intended to cover all effective compositions. For example, if a metal cation is used as the binding agent, then the poorly absorbable antibiotic to metal cation molar ratio can be from about 10:1 to 1:5, preferably about 5:1. Additionally, the poorly absorbable antibiotic to biopolymer molar ratio can be from about 5:1 to 1:5, preferably about 2:1. Alternatively, if a cationic molecule is used as the binding agent, then the poorly absorbable antibiotic to cationic molecule molar ratio can be from about 1:4 to 1:1, preferably from about 1:2 to 1:1, e.g., 1:2 for antibiotic:amino acid embodiments and 1:1 for antibiotic:cetyl pyridinium embodiments. Additionally, in this embodiment, the poorly absorbable antibiotic to biopolymer molar ratio can be from about 5:1 to 1:5, preferably about 2:1.

In the above compositions and methods, the biopolymer for use may be any biopolymer that is functional with the present invention. However, when in the form of a hydrogel, mucoadhesive and/or swellable biopolymers are the most preferred. Exemplary biopolymers include, but are not limited to carrageenan, pectin, chondroitin sulfate, sodium alginate, and/or poly(methacrylic acid).

Poorly absorbable antibiotics can include any antibiotic that, in the absence of being part of a composition of the present invention, is substantially inhibited from crossing the mucosal membrane of the intestines. However, poorly absorbable antibiotics with which the technology of the present invention is particularly useful include many charged cephalosporins, charged peptide and polypeptide antibiotics, and/or charged aminoglycosides.

If a charged cephalosporin is used, third generation cephalosporins are included among exemplary poorly absorbable antibiotics that may be used. Specific examples of functional cephalosporins for use with the present invention include, but are not limited to, ceftiofur, cefepime, cefixime, cefoperazone, cefotaxime, cefpodoxime, ceftazidime, ceftizoxime, ceftriaxone, and/or moxalactam. If an aminoglycoside is used, functional drugs include amikacin and/or tobramycin. If a peptide or polypeptide antibiotic is used, then vancomycin, daptomycin, polymixin-B, and/or bacitracin can also be functional.

In accordance with the first embodiment, if a metal cation is used as the binding agent, calcium, potassium, magnesium, iron, copper, zinc, aluminum, manganese, chromium, cobalt, nickel, and/or sodium may be used. These cations are preferred because each of these metal cations are biocompatible. However, cations such as zinc, and particularly, calcium are most preferred.

The metal cation can be arranged in relation to the biopolymer and the poorly absorbable antibiotic in one of three preferred manners. First, the metal cation can be bound to the biopolymer forming a cation-biopolymer combination such that the antibiotic is entrained within the cationic-biopolymer ionic combination. Second, the metal cation can be complexed to the antibiotic and the cation-antibiotic complex can then be entrained within the biopolymer. Third, the metal cation can be complexed to the antibiotic and further bound to the biopolymer forming an antibiotic-cation-biopolymer bridge. When using the metal cation as the binding agent, the compositions of the present invention may be prepared in both solid form (e.g., tablets, capsules, etc.) and suspension form.

If a cationic molecule is used as the binding agent (rather than the metal cation), then there are three preferred molecule types that may be used. First, cationic polymers including, but not limited to, poly(allylamine), poly-(l-lysine), poly(arginine), dodecyl trimethyl ammonium bromide, and/or polyethylenimines (primary, secondary, and tertiary) may be used. Additionally, basic amino acids may be used as the cationic molecule. Exemplary basic amino acids include the use of one or more of the naturally occurring amino acids such as arginine, lysine, and/or histidine. Further, the cationic molecule may be a quaternary ammonium salt including, but not limited to, benzalkonium derivatives, cetyl pyridinium derivatives such as chlorides or bromides, dodecyl-trimethyl ammonium salt derivatives, tetradecyl-trimethyl ammonium salt derivatives, and/or cetyl-trimethyl ammonium salt derivatives.

No matter which cationic molecule is used, the cationic molecule can be arranged in relation to the biopolymer and the poorly absorbable antibiotic in one of two preferred manners. First, the cationic molecule can be bound to the biopolymer forming a cationic molecule-biopolymer combination and the antibiotic can be entrained within the cationic molecule-biopolymer combination. Second, the cationic molecule can be bound to the antibiotic forming a cationic molecule-antibiotic combination and the cationic molecule-antibiotic combination can be entrained within the biopolymer.

The compositions of the present invention may be administered orally in a solid state such as in a capsule or tablet or may be delivered orally as a suspension, depending on the formulation used. In either case, the composition is designed such that the antibiotic may be transmucosally delivered into the bloodstream, preferably through the walls of the small intestines.

EXAMPLES

The following examples illustrate the preferred embodiments of the invention that are presently best known. Thus, these examples should not be considered as limitations of the present invention, but are merely in place to teach how to make the best known compositions of the present invention based upon current experimental data.

Preparation of Various Complexes of the Present Invention

EXAMPLE 1

Preparation of Ceftriaxone-calcium-carrageenan Complex

About 400 mg of carrageenan was added to 80 ml of an aqueous solution containing 1.0 g (1.67 mmole) of ceftriaxone. The solution was then mixed by magnetic stirrer at room temperature until the carrageenan was essentially fully swollen, forming a ceftriaxone-carrageenan hydrogel. Next, an aqueous solution containing $Ca^{2+}$ ions was prepared by dissolving 48.5 mg (0.33 mole) of calcium chloride in 20 ml of water. The entire aqueous solution was then dropped into the ceftriaxone-carrageenan hydrogel. The complex was then stirred by a magnetic stirrer at room temperature for 2 hours. This resulted in the formation of a ceftriaxone-calcium-carrageenan gel complex. The ceftriaxone-calcium-carrageenan gel complex was then freeze-dried while in the swollen state. About 1.4 grams of a ceftriaxone-calcium-carrageenan was obtained in a freeze dried state.

EXAMPLE 2

Preparation of a Ceftriaxone-zinc-carrageenan Complex

About 400 mg of carrageenan was added to 80 ml of an aqueous solution containing 1.0 g (1.67 mole) of ceftriaxone. The solution was then mixed by magnetic stirrer at room temperature until the carrageenan was essentially fully swollen, forming a ceftriaxone-carrageenan hydrogel. Next, an aqueous solution containing zinc ions was prepared by dissolving 45 mg (0.33 mole) of zinc chloride in 20 ml of water. The entire aqueous solution was then dropped into the ceftriaxone-carrageenan hydrogel or suspension. The complex was then stirred by a magnetic stirrer at room temperature for 2 hours. This resulted in the formation of a ceftriaxone-zinc-carrageenan gel complex. The ceftriaxone-zinc-carrageenan gel was then freeze-dried while in the swollen state. About 1.4 grams of a ceftriaxone-zinc-carrageenan complex was obtained.

EXAMPLE 3

Preparation of a Ceftriaxone-arginine-carrageenan Complex

About 582 mg (3.34 mole) of particulate arginine was dissolved in 50 ml of distilled water. Additionally, about 1.0 grams (1.67 mole) of ceftriaxone was dissolved in 50 ml of a separate volume of distilled water. The solution containing arginine was adjusted with 1N-HCl until the pH reached 6.0. The ceftriaxone solution was then added to the arginine solution and stirred by a magnetic stirrer at room temperature for 1 hour forming a ceftriaxone-arginine solution. To the ceftriaxone-arginine solution was added about 400 mg of carrageenan and the solution was stirred by magnetic stirrer at room temperature for 2 hours. A ceftriaxone-arginine-carrageenan complex was formed which was freeze-dried while in the swollen state, yielding about 1.84 g of the freeze dried complex.

EXAMPLE 4

Preparation of a Ceftriaxone-lysine-carrageenan Complex

About 610 mg (3.34 mole) of particulate lysine was dissolved in 50 ml of distilled water. Additionally, 1.0 gram (1.67 mole) of ceftriaxone was dissolved in 50 ml of a separate volume of distilled water. The solution containing arginine was adjusted with 1N-HCl until the solution reached pH 6.0. The ceftriaxone solution was then added to the lysine solution and stirred by a magnetic stirrer at room temperature for 1 hour forming a ceftriaxone-lysine solution. To the ceftriaxone-lysine solution was added about 400 mg of carrageenan and the solution was stirred by magnetic stirrer at room temperature for 2 hours. A ceftriaxone-lysine-carrageenan hydrogel was formed. The hydrogel was then freeze-dried while in the swollen state, yielding about 1.92 g of the freeze dried complex.

EXAMPLE 5

Preparation of Ceftriaxone-histidine-carrageenan Complex

About 518.4 mg (3.34 mole) of histidine was dissolved in 50 ml of distilled water. Additionally, about 1.0 grams (1.67 mole) of ceftriaxone was dissolved in 50 ml of a separate volume of distilled water. The solution containing histidine was adjusted with 1N-HCl until the solution reached pH 5.5. Next, the ceftriaxone solution was added to the histidine solution and stirred by a magnetic stirrer at room temperature for 1 hour forming a ceftriaxone-histidine complex solution. About 400 mg of carrageenan was added to ceftriaxone-histidine solution and stirred by magnetic stirrer at room temperature for 2 hours forming a hydrogel. After the stirring was complete, a white suspension was formed in the hydrogel. The ceftriaxone-histidine-carrageenan hydrogel in a swollen state was rapidly freeze-dried using a dry-ice-acetone mixture. About 1.75 g of product was produced.

EXAMPLE 6

Preparation of a Ceftriaxone-cetyl Pyridinium chloride-carrageenan Complex

About 210 mg (0.62 mole) of particulate cetyl pyridinium chloride was dissolved in 50 ml of distilled water. Additionally, about 378 mg (0.62 mole) of ceftriaxone was dissolved in 50 ml of a separate volume of distilled water. Next, the ceftriaxone solution was added to the cetyl pyridinium chloride solution and stirred by a magnetic stirrer at room temperature for 1 hour forming a ceftriaxone-cetyl pyridinium chloride solution. About 400 mg of carrageenan was added to the ceftriaxone-cetyl pyridinium chloride solution and the solution was stirred by magnetic stirrer at room temperature for 2 hours. A ceftriaxone-cetyl pyridinium chloride-carrageenan hydrogel complex was formed. The complex was then freeze-dried while in the swollen state, yielding about 0.86 g of the freeze dried complex.

Absorption of Otherwise Poorly Absorbable Antibiotics Using Compositions of the Present Invention A representative number of examples are described herein showing the absorption of ceftriaxone over time in rats after intraduodenal (i.d.) administration. Though i.d. administration is exemplified, acceptable results can be likewise obtained after oral administration.

Additionally, though the data of Tables 2 and 4 below appear to be similar to the control (See Table 6 of Example 12 below where CTX is administered with capmul), it should be noted that these examples are i.d. examples. Part of the purpose of the present invention is to provide complexes that are stable as oral dosage forms. Thus, in the acidic environment of the stomach, the complexes described as part of the present invention (including Examples 7–11) are generally more stable in the acidic environment of the stomach than the composition described in the control (Example 12).

EXAMPLE 7

Plasma Concentration of Ceftriaxone Over Time in Rats After Intraduodenal (i.d.) Administration of a Ceftriaxone-calcium-carrageenan Complex About 40 mg ceftriaxone (CTX) eq./kg of the complex described in Example 1 was suspended in water and i.d. administered with 0.2 ml of capmul (an absorption enhancer) to four rats. At specific time intervals, 0.6 ml of blood was taken from each rat and centrifuged. About 0.2 ml of the blood plasma was then analyzed for CTX by HPLC. The results are represented in Table 1 below:

TABLE 1

| Time After i.d. Dosage (minutes) | Average Plasma Concentration of CTX (µg/ml) |
|---|---|
| 30 | 53 |
| 60 | 40 |
| 90 | 33 |
| 120 | 25 |
| 180 | 14 |
| 240 | 9 |

Thus, by administering an otherwise poorly absorbable antibiotic (CTX) to rats as part of the composition described in Example 1, greater antibiotic absorption was realized than that disclosed in the control.

EXAMPLE 8
Plasma Concentration of Ceftriaxone Over Time in Rats After Intraduodenal (i.d.) Administration of a Ceftriaxone-zinc-carrageenan Complex About 40 mg CTX eq./kg of the complex described in Example 2 was suspended in water and i.d. administered with 0.2 ml of capmul to four rats. At specific time intervals, 0.6 ml of blood was taken from each rat and centrifuged. About 0.2 ml of the blood plasma was then analyzed for CTX by HPLC. The results are represented in Table 2 below:

TABLE 2

| Time After i.d. Dosage (minutes) | Average Plasma Concentration of CTX (µg/ml) |
|---|---|
| 30 | 17 |
| 60 | 16 |
| 90 | 17 |
| 120 | 13 |
| 180 | 14 |
| 240 | 8 |

By administering an otherwise poorly absorbable antibiotic (CTX) to rats as part of the composition described in Example 2, slightly enhanced absorption over the control of Example 12 was realized. However, it should be noted that these examples are i.d. examples. Thus, in an oral dosage form, the composition described in Example 2 may better survive the acidic environment of the stomach than the composition described in the control example.

EXAMPLE 9
Plasma Concentration of Over Time in Rats After Intraduodenal (i.d.) Administration of a Ceftriaxone-arginine-carrageenan Complex About 40 mg CTX eq./kg of the complex described in Example 3 was suspended in water and i.d. administered with 0.2 ml of capmul to four rats. At specific time intervals, 0.6 ml of blood was taken from each rat and centrifuged. About 0.2 ml of the blood plasma was then analyzed for CTX by HPLC. The results are represented in Table 3 below:

TABLE 3

| Time After i.d. Dosage (minutes) | Average Plasma Concentration of CTX (µg/ml) |
|---|---|
| 30 | 57 |
| 60 | 39 |

TABLE 3-continued

| Time After i.d. Dosage (minutes) | Average Plasma Concentration of CTX (µg/ml) |
|---|---|
| 90 | 26 |
| 120 | 20 |
| 180 | 13 |
| 240 | 9 |

Thus, by administering CTX to rats as part of the composition described in Example 3, greater antibiotic absorption was realized than that disclosed in the control.

EXAMPLE 10
Plasma Concentration of Ceftriaxone Over Time in Rats After Intraduodenal (i.d.) Administration of a Ceftriaxone-lysine-carrageenan Complex About 40 mg CTX eq./kg of the complex described in Example 4 was suspended in water and i.d. administered with 0.2 mol of capmul to four rats, At specific time intervals, 0.6 ml of blood was taken from each rat and centrifuged. About 0.2 ml of the blood plasma was then analyzed for CTX by HPLC. The results are represented in Table 4 below:

TABLE 4

| Time After i.d. Dosage (minutes) | Average Plasma Concentration of CTX (µg/ml) |
|---|---|
| 30 | 14 |
| 60 | 6 |
| 90 | 5 |
| 120 | 4 |
| 180 | 3 |
| 240 | 2 |

By administering an otherwise poorly absorbable antibiotic (CTX) to rats as part of the composition described in Example 4, slightly enhanced initial absorption over the control of Example 12 was realized at 30 minutes. At 60 to 240 minutes, the control showed better absorption than the composition of Example 4. However, it should be noted that these examples are i.d. examples. Thus, in an oral dosage form, the composition described in Example 2 may better survive the acidic environment of the stomach than the composition described in the control example. Thus, after 60 minutes, even the composition of Example 4 may produce superior results than the control composition in some applications.

EXAMPLE 11
Plasma Concentration of Ceftriaxone Over Time in Rats After Intraduodenal (i.d.) Administration of the Ceftriaxone-cetyl Pyridinium Chloride-carrageenan About 40 mg CTX eq./kg of the complex described in Example 6 was suspended in water and i.d. administered without capmul to four rats. At specific time intervals, 0.6 ml of blood was taken from each rat and centrifuged. About 0.2 ml of the blood plasma was then analyzed for CTX by HPLC. The results are represented in Table 5 below:

TABLE 5

| Time After i.d. Dosage (minutes) | Average Plasma Concentration of CTX (μg/ml) |
| --- | --- |
| 30 | 28 |
| 60 | 30 |
| 90 | 29 |
| 120 | 27 |
| 180 | 25 |
| 240 | 21 |

By administering CTX to rats as part of the composition described in Example 6, greater antibiotic absorption was realized than that disclosed in the control.

EXAMPLE 12

Plasma Concentration of Ceftriaxone Over Time in Rats After Intraduodenal (i.d.) Administration of the CTX with Capmul as Described in the Prior Art As a control, about 40mg/kg of CTX was i.d. co-administered with 0.2 ml of capmul to four rats. See, Chemotherapy 34: 77–84 (1988). At specific time intervals, 0.6 ml of blood was taken from each rat and centrifuged. About 0.2 ml of the blood plasma was then analyzed for CTX by HPLC. The results are represented in Table 6 below:

TABLE 6

| Time After i.d. Dosage (minutes) | Average Plasma Concentration of CTX (μg/ml) |
| --- | --- |
| 30 | 10 |
| 60 | 11 |
| 90 | 9 |
| 120 | 7 |
| 180 | 6 |
| 240 | 5 |

Based upon the data described in Examples 7–11 above, the composition of the present invention are shown to enhance the ability of CTX to enter the blood plasma through the intestinal epithelium walls comparably, or in many instances, even better than does the composition described in Example 12 after i.d. administration.

EXAMPLE 13

Plasma Concentration of Ceftriaxone Over Time in Rats After i.v. Administration

For comparison purposes, about 20mg/kg of CTX was administered (i.v.) to four rats. At specific time intervals, 0.6 ml of blood was taken from each rat and centrifuged. About 0.2 ml of the blood plasma was then analyzed for CTX by HPLC. The results are shown in Table 7 below:

TABLE 7

| Time After i.v. Dosage (minutes) | Average Plasma Concentration of CTX (μg/ml) |
| --- | --- |
| 5 | 211 |
| 15 | 89 |
| 30 | 66 |
| 60 | 45 |
| 90 | 37 |
| 120 | 30 |

TABLE 7-continued

| Time After i.v. Dosage (minutes) | Average Plasma Concentration of CTX (μg/ml) |
| --- | --- |
| 180 | 19 |
| 240 | 12 |

Though the initial concentration in the blood plasma after i.v. injection was very high, after 30 minutes, the concentration of CTX in the plasma was comparable to the concentrations found in the plasma after i.d. administering the CTX as described in Examples 7, 9, and 11.

While this invention has been particularly shown and described with references to a few preferred embodiments, it will be understood by those skilled in the art that various changes in form and details may be made therein without departing from the spirit and scope of the invention as defined by the appended claims.

What is claimed is:

1. A pharmaceutical composition for oral delivery comprising:
   a) a biopolymer;
   b) a poorly absorbable antibiotic contained within or ionically bound to the biopolymer; and
   c) a metal cation ionically bound to at least one member selected from the group consisting of the biopolymer and the antibiotic.

2. The pharmaceutical composition of claim 1 wherein the biopolymer, when hydrated, is mucoadhesive.

3. The pharmaceutical composition of claim 1 wherein the biopolymer, when hydrated, is swellable.

4. The pharmaceutical composition of claim 1 wherein the poorly absorbable antibiotic and metal cation are present at a molar ratio of from about 10:1 to 1:5.

5. The pharmaceutical composition of claim 4 wherein the poorly absorbable antibiotic to metal cation molar ratio is about 5:1.

6. The pharmaceutical composition of claim 1 wherein the poorly absorbable antibiotic and biopolymer are present at a molar ratio from about 5:1 to 1:5.

7. The pharmaceutical composition of claim 6 wherein the poorly absorbable antibiotic to biopolymer molar ratio is about 2:1.

8. The pharmaceutical composition of claim 1 wherein the biopolymer is selected from the group consisting of carrageenan, pectin, chondroitin sulfate, sodium alginate, poly(methacrylic acid), and combinations thereof.

9. The pharmaceutical composition of claim 1 wherein the poorly absorbable antibiotic is selected from the group consisting of charged cephalosporins, charged peptide and polypeptide antibiotics, charged aminoglycosides, and combinations thereof.

10. The pharmaceutical composition of claim 9 wherein the charged cephalosporin is a third generation cephalosporin.

11. The pharmaceutical composition of claim 10 wherein the third generation cephalosporin is selected from the group consisting of ceftiofur, cefepime, cefixime, cefoperazone, cefotaxime, cefpodoxime, ceftazidime, ceftizoxime, ceftriaxone, moxalactam, and combinations thereof.

12. The pharmaceutical composition of claim 9 wherein the charged aminoglycoside is selected from the group consisting of amikacin, tobramycin, and combinations thereof.

13. The pharmaceutical composition of claim 9 wherein the charged peptide or polypeptide antibiotic is selected from the group consisting of vancomycin, daptomycin, polymixin-B, bacitracin, and combinations thereof.

14. The pharmaceutical composition of claim 1 wherein the metal cation is selected from the group consisting of calcium, potassium, magnesium, iron, copper, zinc, aluminum, manganese, chromium, cobalt, nickel, sodium, and combinations thereof.

15. The pharmaceutical composition of claim 14 wherein the metal cation is calcium.

16. The pharmaceutical composition of claim 14 wherein the metal cation is zinc.

17. The pharmaceutical composition of claim 1 wherein the metal cation is tonically bound to the biopolymer forming a metal cation-biopolymer combination and the antibiotic is entrained within the metal cation-biopolymer combination.

18. The pharmaceutical composition of claim 1 wherein the metal cation is complexed to the antibiotic forming a metal cation-antibiotic complex and the metal cation-antibiotic complex is entrained within the biopolymer.

19. The pharmaceutical composition of claim 1 wherein the metal cation is complexed to the antibiotic and the metal cation is further ionically bound to the biopolymer forming an antibiotic-metal cation-biopolymer bridge.

20. The pharmaceutical composition of claim 1 wherein the biopolymer is carrageenan, the antibiotic is ceftriaxone, and the metal cation is calcium.

21. The pharmaceutical composition of claim 1 wherein the biopolymer is carrageenan, the antibiotic is ceftriaxone, and the metal cation is zinc.

22. The pharmaceutical composition of claim 1 wherein the composition is a suspension for oral delivery.

23. The pharmaceutical composition of claim 1 wherein the composition is in a solid oral dosage form.

24. A pharmaceutical composition for oral delivery comprising:
  a) a biopolymer;
  b) a poorly absorbable antibiotic contained within or ionically bound to the biopolymer; and
  c) a cationic molecule tonically bound to at least one member selected from the group consisting of the biopolymer and the antibiotic.

25. The pharmaceutical composition of claim 24 wherein the biopolymer, when hydrated, is mucoadhesive.

26. The pharmaceutical composition of claim 24 wherein the biopolymer, when hydrated, is swellable.

27. The pharmaceutical composition of claim 24 wherein the poorly absorbable antibiotic and cationic molecule are present at a molar ratio of from about 1:4 to 1:1.

28. The pharmaceutical composition of claim 27 wherein the poorly absorbable antibiotic to cationic molecule molar ratio is from about 1:2 to 1:1.

29. The pharmaceutical composition of claim 24 wherein the poorly absorbable antibiotic and biopolymer are present at a molar ratio from about 5:1 to 1:5.

30. The pharmaceutical composition of claim 29 wherein the poorly absorbable antibiotice to biopolymer molar ratio is about 2:1.

31. The pharmaceutical composition of claim 24 wherein the biopolymer is selected from the group consisting of carrageenan, pectin, chondroitin sulfate, sodium alginate, poly(methacrylic acid), and combinations thereof.

32. The pharmaceutical composition of claim 24 wherein the poorly absorbable antibiotic is selected from the group consisting of charged cephalosporins, charged peptide and polypeptide antibiotics, charged aminoglycosides, and combinations thereof.

33. The pharmaceutical composition of claim 32 wherein the charged cephalosporin is a third generation cephalosporin.

34. The pharmaceutical composition of claim 33 wherein the third generation cephalosporin is selected from the group consisting of ceftiofur, cefepime, cefixime, cefoperazone, cefotaxime, cefpodoxime, ceftazidime, ceftizoxime, ceftriaxone, moxalactam, and combinations thereof.

35. The pharmaceutical composition of claim 32 wherein the charged aminoglycoside is selected from the group consisting of amikacin, tobramycin, and combinations thereof.

36. The pharmaceutical composition of claim 32 wherein the charged peptide or polypeptide antibiotic is selected from the group consisting of vancomycin, daptomycin, polymixin-B, bacitracin, and combinations thereof.

37. The pharmaceutical composition of claim 24 wherein the cationic molecule is selected from the group consisting of cationic polymers, basic amino acids, quaternary ammonium salts, and combinations thereof.

38. The pharmaceutical composition of claim 37 wherein the cationic molecule is a cationic polymer.

39. The pharmaceutical composition of claim 37 wherein the cationic molecule is a basic amino acid.

40. The pharmaceutical composition of claim 37 wherein the cationic molecule is a quaternary ammonium salt.

41. The pharmaceutical composition of claim 38 wherein the cationic polymer is selected from the group consisting of poly(allylamine), poly-(L-lysine), poly-(L-arginine), dodecyl trimethyl ammonium bromide, polyethylenimines (primary, secondary, and tertiary), and combinations thereof.

42. The pharmaceutical composition of claim 39 wherein the basic amino acid is selected from the group consisting of arginine, lysine, histidine, and combinations thereof.

43. The pharmaceutical composition of claim 40 wherein the quaternary ammonium salt is selected from the group consisting of benzalkonium derivatives, cetyl pyridinium derivatives, dodecyl-trimethyl ammonium salt derivatives, tetradecyl-trimethyl ammonium salt derivatives, cetyl-trimethyl ammonium salt derivatives, and combinations thereof.

44. The pharmaceutical composition of claim 24 wherein the cationic molecule is tonically bound to the biopolymer forming a cationic molecule-biopolymer combination and the antibiotic is entrained within the cationic molecule-biopolymer combination.

45. The pharmaceutical composition of claim 24 wherein the cationic molecule is tonically bound to the antibiotic forming a cationic molecule-antibiotic combination and the cationic molecule-antibiotic combination is entrained within the biopolymer.

46. The pharmaceutical composition of claim 24 wherein the biopolymer is carrageenan, the antibiotic is ceftriaxone, and the cationic molecule is arginine.

47. The pharmaceutical composition of claim 24 wherein the biopolymer is carrageenan, the antibiotic is ceftriaxone, and the cationic molecule is lysine.

48. The pharmaceutical composition of claim 24 wherein the biopolymer is carrageenan, the antibiotic is ceftriaxone, and the cationic molecule is cetyl pyridinium chloride.

49. The pharmaceutical composition of claim 24 wherein the biopolymer is carrageenan, the antibiotic is ceftriaxone, and the cationic molecule is selected from the group consisting of poly(ethylenimine), dodecyl trimethyl ammonium bromide, and combinations thereof.

50. The pharmaceutical composition of claim 24 wherein the composition is a solid oral dosage form.

51. A method of delivering a poorly absorbable antibiotic to the blood stream of an animal comprising the steps of:
   a) orally administering to said animal a composition comprising a biopolymer, an effective amount of a poorly absorbable antibiotic contained within or ionically bound to said biopolymer, and a cationic binding agent ionically bound to at least one member selected from the group consisting of the biopolymer and the antibiotic;
   b) causing the biopolymer to swell and adhere to a mucosal membrane lining of an intestinal wall of said animal; and
   c) delivering the antibiotic from said composition to the mucosal membrane lining such that the antibiotic, and optionally the binding agent, cross the intestinal wall and enter the bloodstream.

52. The method of claim 51 wherein the cationic binding agent is selected from the group consisting of metal cations, cationic polymers, basic amino acids, quaternary ammonium salts, and combinations thereof.

53. The method of claim 51 wherein the biopolymer is selected from the group consisting of carrageenan, pectin, chondroitin sulfate, sodium alginate, poly(methacrylic acid), chitosan, and combinations thereof.

54. The method of claim 51 wherein the poorly absorbable antibiotic is selected from the group consisting of charged cephalosporins, charged peptide and polypeptide antibiotics, charged aminoglycosides, and combinations thereof.

55. The method of claim 54 wherein the charged cephalosporin is a third generation cephalosporin.

56. The method of claim 55 wherein the third generation cephalosporin is selected from the group consisting of ceftiofur, cefepime, cefixime, cefoperazone, cefotaxime, cefpodoxime, ceftazidime, ceftizoxime, ceftriaxone, moxalactam, and combinations thereof.

57. The method of claim 54 wherein the charged aminoglycoside is selected from the group consisting of amikacin, tobramycin, and combinations thereof.

58. The method of claim 54 wherein the charged peptide or polypeptide antibiotic is selected from the group consisting of vancomycin, daptomycin, polymixin-B, bacitracin, and combinations thereof.

59. The method of claim 51 further comprising the preliminary step of preparing a suspension of the biopolymer having the poorly absorbable antibiotic and the cationic binding agent contained within the biopolymer for oral delivery.

60. The method of claim 51 further comprising the preliminary step of preparing a solid dose containing the biopolymer having the poorly absorbable antibiotic and the cationic binding agent contained within the biopolymer for oral delivery.

* * * * *